United States Patent
Stache et al.

(10) Patent No.: US 10,093,765 B2
(45) Date of Patent: Oct. 9, 2018

(54) ALKOXYSILANE-FUNCTIONALIZED ALLOPHANATES

(71) Applicant: Evonik Degussa GmbH, Essen (DE)

(72) Inventors: Wiebke Stache, Herten (DE); Tobias Unkelhäusser, Dülmen (DE); Emmanouil Spyrou, Schermbeck (DE); Annegret Lilienthal, Dorsten (DE); Iris Brückner, Dorsten (DE); Jan Pfingsten, Castrop-Rauxel (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/622,159

(22) Filed: Jun. 14, 2017

(65) Prior Publication Data

US 2017/0369626 A1    Dec. 28, 2017

(30) Foreign Application Priority Data

Jun. 27, 2016 (EP) .................... 16176308

(51) Int. Cl.
| | | |
|---|---|---|
| *C08G 18/10* | (2006.01) | |
| *C08G 18/28* | (2006.01) | |
| *C08G 18/78* | (2006.01) | |
| *C08G 18/71* | (2006.01) | |
| *C09D 175/04* | (2006.01) | |
| *C08G 18/22* | (2006.01) | |
| *C07F 7/18* | (2006.01) | |
| *C08G 18/08* | (2006.01) | |

(52) U.S. Cl.
CPC .......... *C08G 18/289* (2013.01); *C07F 7/1872* (2013.01); *C08G 18/0823* (2013.01); *C08G 18/10* (2013.01); *C08G 18/222* (2013.01); *C08G 18/718* (2013.01); *C08G 18/7837* (2013.01); *C09D 175/04* (2013.01)

(58) Field of Classification Search
None
See application file for complete search history.

(56) References Cited

U.S. PATENT DOCUMENTS

| | | | | |
|---|---|---|---|---|
| 3,903,052 A * | 9/1975 | Wagner | ............... | C08G 18/798 528/21 |
| 4,036,813 A * | 7/1977 | Hardman | ................ | C08L 83/04 524/188 |
| 4,650,835 A * | 3/1987 | Eck | ...................... | C07F 7/1836 525/440.03 |
| 5,220,047 A * | 6/1993 | Pohl | ........................ | C03C 17/30 556/420 |
| 5,990,345 A * | 11/1999 | Lohmann | .............. | C07C 263/04 560/215 |
| 6,319,311 B1 * | 11/2001 | Katz | ..................... | C08G 18/289 106/287.11 |
| 7,060,849 B1 * | 6/2006 | Childress | .............. | C07F 7/1892 556/414 |
| 7,812,087 B2 | 10/2010 | Ludewig et al. | | |
| 8,067,522 B2 | 11/2011 | Ludewig et al. | | |
| 8,163,390 B2 | 4/2012 | Gruber et al. | | |
| 9,040,622 B2 * | 5/2015 | Boghossian | ............ | B32B 15/02 524/589 |
| 2002/0016486 A1 * | 2/2002 | Pinske | ..................... | C07F 7/083 556/411 |
| 2004/0077778 A1 * | 4/2004 | Hazan | ................... | C08G 18/289 524/589 |
| 2009/0286901 A1 * | 11/2009 | Vijverberg | ............ | C09C 1/3081 523/206 |
| 2010/0010113 A1 | 1/2010 | Schwalm et al. | | |
| 2011/0082273 A1 | 4/2011 | Laas et al. | | |
| 2013/0245194 A1 * | 9/2013 | Huang | ................... | C08G 18/10 524/588 |
| 2015/0126678 A1 * | 5/2015 | Kramer | .............. | C08G 18/4866 524/590 |
| 2015/0191625 A1 | 7/2015 | Lomoelder et al. | | |
| 2016/0115351 A1 * | 4/2016 | Iezzi | ................... | C08G 18/3821 524/588 |

(Continued)

FOREIGN PATENT DOCUMENTS

| | | | | |
|---|---|---|---|---|
| DE | 102005041953 A1 | 3/2007 | | |
| DE | 102005041954 A1 | 3/2007 | | |
| DE | 102009047964 A1 | 4/2011 | | |
| EP | 0848024 A1 | 6/1998 | | |
| EP | 3162807 | * 3/2017 | ............... | C07F 7/18 |
| PL | 211785 | * 1/2010 | ............. | C08L 75/04 |
| WO | 2008043722 A1 | 4/2008 | | |
| WO | 2013189882 A2 | 12/2013 | | |

(Continued)

OTHER PUBLICATIONS

Kozakiewicz et al. "New family of functionalized crosslinkers for heat-curable polyurethane systems-A preliminary study" Progress in Organic Coatings, 2011, 72, 120-130. (Year: 2011).*

(Continued)

*Primary Examiner* — Robert S Loewe
(74) *Attorney, Agent, or Firm* — Nexsen Pruet, PLLC; Philip P. McCann

(57) ABSTRACT

The present invention relates to alkoxysilane-functionalized allophanates, to methods for production thereof, and to the use thereof. In particular, the alkoxysilane-functionalized allophanate includes the reaction product of A) at least one alkoxysilane group-containing monourethane A) of the formula 1

$$R_n(OR^1)_{3-n}Si-R^2-NH-(C=O)-OR^3 \quad \text{formula 1,}$$

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B), in a molar ratio of A) to B) of 3:1 to 1.5:1.

21 Claims, No Drawings

(56) References Cited

U.S. PATENT DOCUMENTS

2016/0200745 A1\*   7/2016   Stanjek ................ C07F 7/1892
556/420

FOREIGN PATENT DOCUMENTS

| WO | 2017071933 A1 | 5/2017 |
| WO | 2017071941 A1 | 5/2017 |

OTHER PUBLICATIONS

European Search Report dated Oct. 28, 2016 in EP 16 17 6308 (1 page).
Stache et al., U.S. Appl. No. 15/614,763, filed Jun. 6, 2017.
Stache et al., U.S. Appl. No. 15/619,897, filed Jun. 12, 2017.
Stache et al., U.S. Appl. No. 15/622,204, filed Jun. 14, 2017.

\* cited by examiner

ALKOXYSILANE-FUNCTIONALIZED ALLOPHANATES

This application claims the benefit of European Application No. 16176308.1 filed on Jun. 27, 2016, the disclosure of which is expressly incorporated herein by reference.

BACKGROUND

The present invention relates to alkoxysilane-functionalized allophanates, to a method for production thereof, and to the use thereof.

Polyurethanes have been established for many decades as high-value components for paint, adhesive, sealant and plastics systems. It is possible here for additional alkoxysilane groups to play an important role, for example with regard to network density, chemical resistance and scratch resistance, primarily through the formation of siloxane and polysiloxane structures.

Molecules both possessing alkoxysilane groups and having isocyanate groups offer the option of introducing the functionalities that are the resulting reaction products, siloxanes and polyurethane groups, by means of one component. Such substances have long been in use, for example in the form of isocyanatoalkyltrialkoxysilanes.

Alkoxysilane-terminated polyurethanes prepared from isocyanatoalkyltrialkoxysilanes and alcohols are also known and are used, for example, for producing highly crosslinked, rigid coating compositions (e.g. WO 2013/189882 A2). However, if these alkoxysilane-terminated polyurethanes are used as sole binder in systems that cure at room temperature, coatings are obtained with only moderate hardness.

There is therefore a need for novel binders that overcome the disadvantage of the prior art.

Allophanate-containing binders have long been known. Alkoxysilane-functionalized allophanates are also known. There are several types that can be distinguished here, which are shown below, but correspond neither in terms of structure nor the application to the alkoxysilane-functionalized allophanates according to the invention.

For instance, the allophanates III (1) described in WO 2008/043722 A1 are obtained by reacting NCO-terminated allophanate-containing polyurethanes I (1) with alkoxysilanes II (1) reactive to isocyanate (e.g. aminoalkyltrialkoxysilane). The allophanate groups here are therefore in the centre of the polyurethane chain and the alkoxysilane function is attached via the terminal isocyanate group in the context of a urea function (structure III (1), equation 1).

(Equation 1)

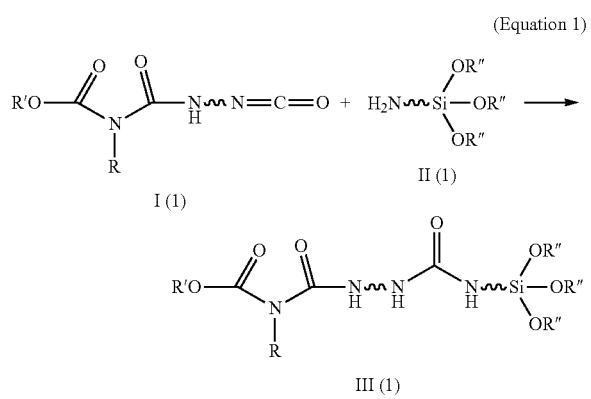

DE 102005041953 A1 describes the reaction of a polyol I (2) having an average molecular weight of 3000-20000 g/mol with an excess of isocyanatopropyltrimethoxysilane II (2), so as to result in formation of an allophanate IV (2) having two alkoxysilane functions per allophanate unit after the polyurethane formation III (2).

(Equation 2)

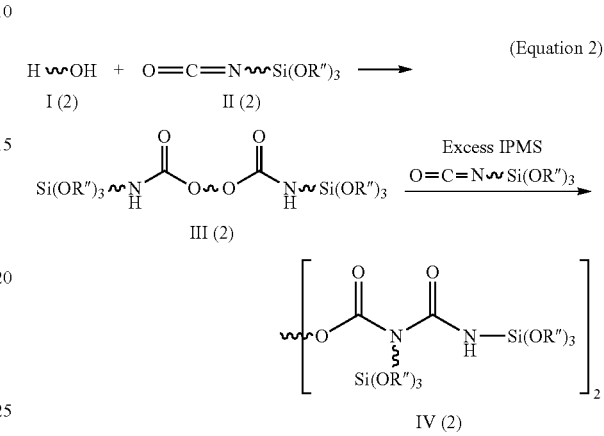

In DE 102005041954 A1, a polyurethane I (3) is treated with isocyanatopropyltrimethoxysilane II (3) and heated, until allophanate structures are formed. In this case, the alkoxysilane group is attached to the terminal nitrogen of the allophanate group (III) (3) (equation 3).

(Equation 3)

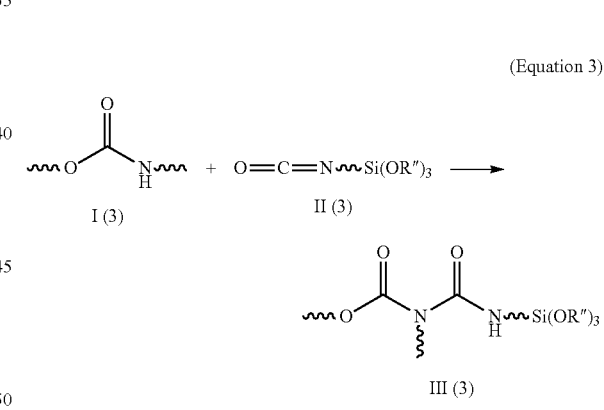

J. Kozakiewicz et al. in *Progress in Organic Coatings* 72 (2011) 120-130 published the reaction of isocyanatopropyltrimethoxysilane I (4) with methanol, to give the corresponding urethane II (4), and subsequently with hexamethylene diisocyanate trimer III (4). In the highly viscous allophanate IV (4) resulting therefrom, the alkoxysilane function is appended on the tertiary central amine of the allophanate group (equation 4).

(Equation 4)

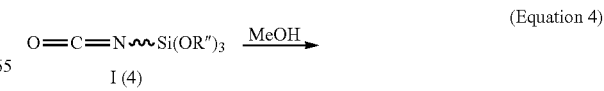

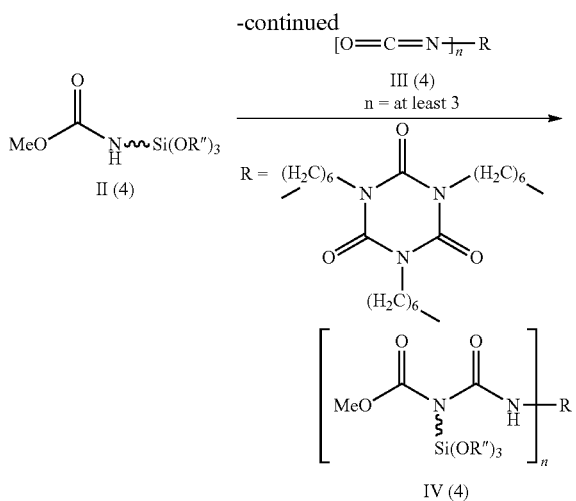

In the use described, the allophanate function serves as blocking agent for the hexamethylene diisocyanate trimer which was used as crosslinker for hydroxy-functionalized polyester polyols.

Even now, there exists a need for novel, silane-containing binders which have specific properties.

SUMMARY

The object of this invention was to make accessible novel silane-containing compounds which are suitable for the development of highly crosslinked, rigid coatings.

This object is achieved by alkoxysilane-functionalized allophanates according to the present invention.

Surprisingly, it was found that the alkoxysilane-functionalized allophanate according to the invention is suitable for use as paint, adhesive or sealant. The alkoxysilane-functionalized allophanate according to the invention may be used particularly for the development of highly crosslinked, particularly rigid coatings. In this case, the alkoxysilane-functionalized allophanate according to the invention may be used as sole binder both in cold and hot curing, even solvent-free if required.

DETAILED DESCRIPTION

The invention relates to alkoxysilane-functionalized allophanates comprising the reaction product of A) at least one, preferably one, alkoxysilane group-containing monourethane A) of the formula 1

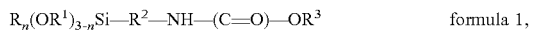

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B), in a molar ratio of A) to B) of from 3:1 to 1.5:1, preferably from 2.5:1 to 1.8:1, particularly preferably 2:1.

Here, alkoxysilane-functionalized allophanates, which comprise the reaction product specified, are understood to mean in particular allophanates which consist of the reaction product of monourethane and diisocyanate itself or which were derivatized or further reacted based on unreacted isocyanate groups potentially in the reaction product. Preferably the reaction product specified is an allophanate which consists of the reaction product of monourethane and diisocyanate itself or which has been derivatized, i.e. reacted or capped, based on unreacted isocyanate groups potentially in the reaction product. Particularly preferably, the reaction product specified is an allophonate which consists of the reaction product of monourethane and diisocyanate itself or which has been reacted with at least one alcohol based on unreacted isocyanate groups potentially in the reaction product.

The allophanates according to the invention, which can be considered as the reaction of at least one monourethane with at least one diisocyanate, are adducts having on average one or two allophanate units, since the diisocynate can react partially or completely with one or two monourethanes. However, the allophonate according to the invention preferably has two allophonate units.

The reaction product is obtained by reacting at least one monourethane with at least one diisocyanate in the stoichiometry specified. Preferably, the reaction product is obtained by reacting one monourethane with at least one diisocyanate in the stoichiometry specified. More preferably, the reaction product is obtained by reacting one monourethane with one diisocyanate in the stoichiometry specified.

"One" monourethane or "one" diisocyanate is understood to mean in this case the empirical formula of the respective monourethane or the respective diisocyanate in each case.

The invention preferably relates to alkoxysilane-functionalized allophanates consisting of the reaction product of A) and B), as defined above, reacted in a molar ratio of A) to B) of 3:1 to 1.5:1, preferably from 2.5:1 to 1.8:1, particularly preferably 2:1.

The invention also relates to alkoxysilane-functionalized allophanates, obtained by reacting A) at least one, preferably one, alkoxysilane group-containing monourethane A) of the formula 1

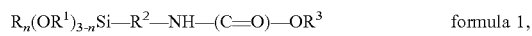

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B),
in a molar ratio of A) to B) of from 3:1 to 1.5:1, preferably from 2.5:1 to 1.8:1, particularly preferably 2:1;

C) optionally in the presence of at least one catalyst C), and

D) optional reaction of the residual amount of NCO groups of B) with an alcohol D).

R, $R^1$, $R^2$ and $R^3$ are preferably at the same time or each independently methyl, ethyl, n-propyl, isopropyl, n-butyl, sec-butyl or tert-butyl.

Preferably, n=0.

$R^1$ and $R^3$ are preferably at the same time or each independently methyl or ethyl.

$R^2$ is preferably methyl or propyl.

Preference is given to compounds where n is 0, $R^1$ and $R^3$ are at the same time or each independently methyl or ethyl, and $R^2$ is at the same time or mutually independently methyl or propyl.

Preferably, $R^3=R^1$.

Preference is given to compounds where n is 0 and $R^2$ is methyl or propyl, and $R^1$ is methyl or ethyl and $R^3=R^1$.

Very particular preference is given to the compound where n is 0, $R^1$ and $R^3$ are methyl and $R^2$ is propyl, N-trimethoxysilylpropylmethyl carbamate.

After the reaction according to the invention of the alkoxysilane group-containing monourethane A) with the diisocyanate B), the NCO content in the end product is preferably <3% by weight, particularly preferably <1% by weight, especially preferably <0.2% by weight.

The diisocyanate B) used in accordance with the invention may be any aliphatic, cycloaliphatic and/or (cyclo)aliphatic diisocyanate. In one preferred embodiment the term "(cyclo)aliphatic diisocyanate" as used herein means that in a molecule there are present simultaneously NCO groups bonded to a ring and NCO groups bonded to an aliphatic radical, as is the case, for example, for isophorone diisocyanate. In one preferred embodiment the term "cycloaliphatic diisocyanate" as used herein refers to a diisocyanate which only has NCO groups bonded directly on the cycloaliphatic ring, e.g. diisocyanatodicyclohexylmethane (H12MDI).

Aliphatic diisocyanates preferably suitable for use as diisocyanate B) include a linear and/or branched alkylene radical having preferably 3 to 16 carbon atoms, more preferably 4 to 12 carbon atoms. Preferably suitable cycloaliphatic or (cyclo)aliphatic diisocyanates include a cycloalkylene radical having preferably 4 to 18 carbon atoms, more preferably 6 to 15 carbon atoms. Preferred examples of suitable diisocyanates include cyclohexane diisocyanate, methylcyclohexane diisocyanate, ethylcyclohexane diisocyanate, propylcyclohexane diisocyanate, methyldiethylcyclohexane diisocyanate, propane diisocyanate, butane diisocyanate, pentane diisocyanate, hexane diisocyanate, heptane diisocyanate, octane diisocyanate, nonane diisocyanate, such as 4-isocyanatomethyl-1,8-octane diisocyanate (TIN), decane di- and triisocyanate, undecane di- and triisocyanate, dodecane di- and triisocyanates. Likewise preferably suitable are 4-methylcyclohexane 1,3-diisocyanate, 2-butyl-2-ethylpentamethylene diisocyanate, 3(4)-isocyanatomethyl-1-methylcyclohexyl isocyanate, 2-isocyanatopropylcyclohexyl isocyanate, 2,4'-methylenebis(cyclohexyl) diisocyanate and/or 1,4-diisocyanato-4-methylpentane.

Preferred diisocyanates B) are isophorone diisocyanate (IPDI), hexamethylene diisocyanate (HDI), 2,2'-dicyclohexylmethane diisocyanate (2,2'-H12MDI), 2,4'-dicyclohexylmethane diisocyanate (2,4'-H12MDI), 4,4'-di cyclohexylmethane diisocyanate (4,4'-H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in a mixture.

In a particularly preferred embodiment, the diisocyanate B) is IPDI and/or 4,4'-H12MDI and/or HDI and/or a mixture of 2,2,4-TMDI and 2,4,4-TMDI.

The invention also relates to a method for preparing alkoxysilane-functionalized allophanates, by reacting
A) at least one, preferably one, alkoxysilane group-containing monourethane A) of the formula 1

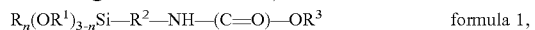
  formula 1, where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and
B) at least one diisocyanate B),
in a molar ratio of A) to B) of from 3:1 to 1.5:1, preferably from 2.5:1 to 1.8:1, particularly preferably 2:1;

C) optionally in the presence of at least one catalyst C), and
D) optional reaction of the residual amount of NCO groups of B) with an alcohol D).

The allophanates according to the invention are generally prepared solventlessly or using non-protic solvents, and the reaction may take place batchwise or continuously. The reaction is conducted in suitable equipment, for example stirred tanks, extruders, static mixers, kneading chambers. The reaction can be conducted at room temperature, i.e. at temperatures in the range of 15 to 40° C., especially in the range of 15 to 25° C. However, preference is given to using higher temperatures in the range from 80 to 220° C., especially in the range from 80 to 120° C. The reaction is conducted with exclusion of water. Preference is given to conducting the reaction solventlessly.

To accelerate the reaction, it is advantageously possible to use catalysts C) known in urethane chemistry, for example organometallic compounds such as tin or zinc compounds, salts, for example Zn(II) chloride, and/or bases. Suitable examples are carboxylates of Sn, Bi, Zn and other metals, for example dibutyltin dilaurate, tin octoate, zinc ethylhexanoate, bismuth neodecanoate, tert-amines, for example 1,4-diazabicyclo[2.2.2]octane (DABCO), 1,8-diazabicyclo[5.4.0]undec-7-ene (DBU), 1,5-diazabicyclo[4.3.0]non-5-ene (DBN), triethylamine, amidine, guanidine, and quaternary ammonium salts, preferably tetraalkylammonium salts, and/or quaternary phosphonium salts.

Useful catalysts C) also include metal acetylacetonates. Examples thereof are zinc acetylacetonate, lithium acetylacetonate, iron acetylacetonate and tin acetylacetonate, alone or in mixtures. Preference is given to using zinc acetylacetonate or zinc ethylhexanoate. Useful catalysts are also quaternary ammonium acetylacetonates or quaternary phosphonium acetylacetonates.

After the reaction according to the invention of the alkoxysilane group-containing monourethane A) with the diisocyanate B), the NCO content is preferably <3% by weight, particularly preferably <1% by weight, especially preferably <0.2% by weight. In the case that the NCO content is between 3% by weight and 0.2% by weight, the residual amounts of NCO groups of B) are reacted with an alcohol D) at the ratio of NCO groups to OH groups of the alcohol D) of from 0.8:1 to 1.2:1, preferably from 0.9:1 to 1.1:1, the stoichiometric reaction i.e. at the ratio of 1:1, being especially preferred. The reaction of the residual amount of NCO groups of B) with an alcohol D) is preferably carried out at temperatures in the range of 30-150° C., in particular in the range of 50-150° C. The reaction is carried out with exclusion of water. Preference is given to conducting the reaction solventlessly.

Preferred alcohols D) used are linear or branched alcohols wherein the hydroxyl function is attached to a primary, secondary or tertiary carbon atom. It is also possible to use diols or polyols. Particular preference is given to methanol, ethanol, propanol, isopropanol, 1-butanol, 2-butanol, pentanol, ethyl-2-hexanol, 1-hexanol. Very particular preference is given to ethanol, propanol and 1-butanol.

The invention also relates to coating compositions and adhesives, comprising or consisting of:
alkoxysilane-functionalized allophanates comprising the reaction product of
A) at least one, preferably one, alkoxysilane group-containing monourethane A) of the formula 1

$R_n(OR^1)_{3-n}Si-R^2-NH-(C=O)-OR^3$      formula 1, where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B), in a molar ratio of A) to B) of from 3:1 to 1.5:1.

Also provided by the invention is the use of the alkoxysilane-functionalized allophanates according to the invention in coating compositions and paint compositions for metal, plastic, glass, wood, MDF (Middle Density Fiberboards) or leather substrates or other heat-resistant substrates.

The invention also provides the use of the alkoxysilane-functionalized allophanates in adhesive compositions for bonding of metal, plastic, glass, wood, MDF or leather substrates or other heat-resistant substrates.

The present invention is more particularly illustrated by the following non-limiting examples from which further features, embodiments, aspects and advantages of the present invention may be discerned.

EXAMPLES

Feedstocks:

Vestanat® EP-UPMS: Trimethoxysilylpropyl methyl carbamate (Evonik Resource Efficiency GmbH)

Vestanat® IPDI: Isophorone diisocyanate (Evonik Resource Efficiency GmbH)

Vestanat® TMDI: Mixture of 2,2,4-trimethylhexamethylene diisocyanate (2,2,4-TMDI) and 2,4,4-trimethylhexamethylene diisocyanate (Evonik Resource Efficiency GmbH)

Vestanat® HT 2500/100: Hexamethylene-1,6-diisocyanate, homopolymer (isocyanurate type) (Evonik Resource Efficiency GmbH)

Vestanat® EP Cat 11 B: Tetraethylammonium benzoate in butanol (Evonik Resource Efficiency GmbH)

Tegoglide® 410: Glide and antiblocking additive based on a polyether siloxane copolymer (Evonik Resource Efficiency GmbH)

1. Preparation

Example 1

Alkoxysilane-Functionalized Allophanate 1

A three-necked flask with reflux condenser was initially charged with 340.2 g of Vestanat® EP-UPMS, 0.3 g of zinc(II) ethylhexanoate and 159.7 g of Vestanat® IPDI, flushed with nitrogen and heated to 100° C. with stirring. After heating for 20 hours, an NCO content of 1.4% by weight NCO was obtained. 10.84 g of butanol were then added and the mixture was heated at 100° C. for 1 h, until an NCO content of <0.1% by weight NCO was reached. After cooling to room temperature, the alkoxysilane-functionalized allophanate 1 according to the invention is obtained as a clear liquid with a viscosity of 14.3 Pas (at 23° C.).

Example 2

Alkoxysilane-Functionalized Allophanate 2

A three-necked flask with reflux condenser was initially charged with 474.6 g of Vestanat® EP-UPMS, 0.22 g of zinc(II) ethylhexanoate and 211.8 g of Vestanat® TMDI, flushed with nitrogen and heated to 100° C. with stirring. After heating for 24 hours, an NCO content of 0.8% by weight NCO was obtained. 10.35 g of butanol were then added and the mixture was heated at 65° C. for 3 h until an NCO content of <0.1% by weight NCO was reached. After cooling to room temperature, the alkoxysilane-functionalized allophanate 2 according to the invention is obtained as a clear liquid with a viscosity of 1170 mPas (at 23° C.).

Comparative Example 3A

Alkoxysilane-Functionalized Allophanate 3A
(Comparative Example)

A three-necked flask with reflux condenser was initially charged with 44.3 g of Vestanat® EP-UPMS, 0.01 g of zinc(II) ethylhexanoate and 35.7 g of Vestanat® HT 2500/100, flushed with nitrogen and heated to 100° C. with stirring until the NCO content of <0.1% by weight was achieved. With continued heating for the purpose of lowering viscosity, 20 g of butyl acetate were then added. The alkoxysilane-functionalized allophanate 3 thus obtained is a clear liquid with a viscosity of 750 mPas (at 23° C.).

Comparative Example 3B

Alkoxysilane-Functionalized Allophonate 3B
(Comparative Example)

A three-necked flask with reflux condenser was initially charged with 335.7 g of Vestanat® EP-UPMS, 0.076 g of zinc(II) ethylhexanoate, 237.8 g of Vestanat® HT 2500/100 and 152 g of xylene, blanketed with nitrogen and heated to 100° C. with stirring until the NCO content of 1% by weight was reached. 13.58 g of butanol were then added and the mixture heated at 100° C. for 0.5 h until an NCO content of <0.1% by weight NCO was reached. The alkoxysilane-functionalized allophanate 3b thus obtained is a clear liquid with a viscosity of 542 mPas (at 23° C.).

2. Preparation of Clearcoats from the Alkoxysilane-Functionalized Allophanates as Coating Compositions For the formulation of the clearcoats according to the invention and the comparative examples, the components of the compositions shown in Table 1 and 2 were mixed directly before processing.

The viscosity of the formulations, determined as the flow time in the DIN 4 cup at 23° C., was approximately 60 seconds.

TABLE 1

Composition of the inventive clearcoats and comparative example of systems curing at room temperature (RT)
Data in % by weight

| Item | | I | II | IIIa (comparative) | IIIb (comparative) |
|---|---|---|---|---|---|
| 1 | Allophanate 1 | 91.24 | | | |
| 2 | Allophanate 2 | | 99.00 | | |
| 3 | Comparative example: Allophanate 3a (comparative) | | | 98.5 | |
| 4 | Comparative example: Allophanate 3b (comparative) | | | | 98.5 |
| 5 | 1,8-Diazabicyclo[5.4.0]undec-7-ene (DBU) | 0.92 | 1.0 | 1.0 | 1.0 |

TABLE 1-continued

Composition of the inventive clearcoats and comparative example of systems curing at room temperature (RT)
Data in % by weight

| Item | | I | II | IIIa (comparative) | IIIb (comparative) |
|---|---|---|---|---|---|
| 6 | Xylene | 7.79 | | 0.45 | 0.45 |
| 7 | Tegoglide 410 | 0.05 | | 0.45 | 0.05 |

Based on the resin, the content of catalyst DBU is 1.0% in examples I and II and 1.25% DBU in example IIIa and b.

TABLE 2

Composition of the inventive clearcoats and comparative example of hot-curing systems
Data in % by weight

| Item | | IV | Va (comparative) | Vb (comparative) |
|---|---|---|---|---|
| 1 | Allophanate 1 | 84.00 | | |
| 2 | Allophanate 2 | | | |
| 3 | Comparative example: Allophanate 3a (comparative) | | 88.53 | |
| 4 | Comparative example: Allophanate 3b (comparative) | | | 88.53 |
| 5 | Vestanat Cat 11 B | 1.71 | 1.45 | 1.45 |
| 6 | Xylene | 14.29 | 10.02 | 10.02 |

Based on the resin, the content of catalyst Vestanat Cat 11 B is 1.0% in all examples.

The mechanical characteristics were determined by applying all of the coating materials to phosphatized steel plates (Chemetall Gardobond 26S/60/OC) using a 100 μm doctor blade and curing them at room temperature (23° C.), Table 3, or at 140° C., Table 4.

TABLE 3

Coating properties of the compositions
I-III after curing at 23° C. (7 days)

| Composition | I | II | IIIa (comparative) | IIIb (comparative) |
|---|---|---|---|---|
| Pendulum hardness (König) [s] n 7 d | 189 | 168 | 158 | 140 |
| MEK test [ASTM D 4752] (Double rubs, 1 kg applied weight) | >150 | >150 | >150 | >150 |
| Appearance of the coating | glossy | glossy | glossy | glossy |

The coating properties of coatings I and II, comprising the inventive alkoxysilane-functionalized allophanate 1 or 2, show significantly higher pendulum hardness than comparative examples IIIa and b. In particular, in the three-fold functionalized product in coating material IIIa and b, a greater hardness would have been expected due to the higher degree of crosslinking.

TABLE 4

Coating properties of the compositions
IV-V after curing at 140° C. (22 min)

| Composition | IV | Va (comparative) | Vb (comparative) |
|---|---|---|---|
| Pendulum hardness (König) [s] n 1 d | 178 | 118 | 59 |
| MEK test [ASTM D 4752] (Double rubs, 1 kg applied weight) | >150 | >150 | >150 |
| Appearance of the coating | glossy | matt | glossy |

The coating properties of coating IV comprising the inventive alkoxysilane-functionalized allophanate 1 shows a significantly higher pendulum hardness than comparative examples V a and b. In particular, in the three-fold functionalized product in coating material V a and b, a greater hardness would have been expected due to the higher degree of crosslinking. In addition, coating IV, with its glossy surface, exhibits a better appearance than the matt coating Va.

The results from Table 3 and 4 show that the inventive alkoxysilane-functionalized allophanates may be used for the development of highly crosslinked, particularly rigid coatings and only these can be used in this case as sole binder both in cold and hot curing, even solvent-free if required.

The invention claimed is:

1. An alkoxysilane-functionalized allophanate comprising the reaction product of A) at least one alkoxysilane group-containing monourethane A) of the formula 1

$$R_n(OR^1)_{3-n}Si-R^2-NH-(C=O)-OR^3 \qquad \text{formula 1,}$$

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and B) at least one diisocyanate B), in a molar ratio of A) to B) of 3:1 to 1.5:1.

2. The alkoxysilane-functionalized allophanate according to claim 1, wherein the molar ratio of A) to B) is from 2.5:1 to 1.8:1.

3. The alkoxysilane-functionalized allophanate according to claim 1, wherein R, $R^1$, $R^2$ and $R^3$ are at the same time or each independently methyl, ethyl, n-propyl, isopropyl, n-butyl, sec-butyl or tert-butyl.

4. The alkoxysilane-functionalized allophanate according to claim 1, wherein n is 0, $R^1$ and $R^3$ are at the same time or each independently methyl or ethyl, and $R^2$ is at the same time or mutually independently methyl or propyl.

5. The alkoxysilane-functionalized allophanate according to claim 1, wherein n is 0 and $R^2$ is methyl or propyl, and $R^1$ is methyl or ethyl and $R^3=R^1$.

6. The alkoxysilane-functionalized allophanate according to claim 1, wherein n is 0, $R^1$ and $R^3$ are methyl and $R^2$ is propyl.

7. The alkoxysilane-functionalized allophanate according to claim 1, wherein the diisocyanate B) is selected from isophorone diisocyanate (IPDI), hexamethylene diisocyanate (HDI), 2,2-di cyclohexylmethane diisocyanate (2,2'-H12MDI), 2,4'-dicyclohexylmethane diisocyanate (2,4'-H12MDI), 4,4'-dicyclohexylmethane diisocyanate (4,4'-

H12MDI), 2-methylpentane diisocyanate (MPDI), pentane diisocyanate, 2,2,4-trimethylhexamethylene diisocyanate (2,2,4-TMDI), 2,4,4-trimethylhexamethylene diisocyanate (2,4,4-TMDI), norbornane diisocyanate (NBDI), methylenediphenyl diisocyanate (MDI), toluidine diisocyanate (TDI), tetramethylxylylene diisocyanate (TMXDI), xylylene diisocyanate (MXDI), individually or in a mixture.

8. The alkoxysilane-functionalized allophanate according to claim 1, wherein the diisocyanate B) is selected from IPDI, 4,4'-H12MDI, HDI and mixtures of 2,2,4-TMDI and 2,4,4-TMDI, individually or in a mixture.

9. A composition, which may be coating compositions and paint compositions for metal, plastic, glass, wood, MDF (Middle Density Fibreboards) or leather substrates or other heat-resistant substrates, the composition comprising the alkoxysilane-functionalized allophanates according to claim 1.

10. An adhesive composition for bonding of metal, plastic, glass, wood, MDF or leather substrates or other heat-resistant substrates, the adhesive composition comprising the alkoxysilane-functionalized allophanates according to claim 1.

11. A coating composition, adhesives or sealant, comprising at least one alkoxysilane-functionalized allophanate according to claim 1.

12. An alkoxysilane-functionalized allophanate, obtained by reacting
A) at least one alkoxysilane group-containing monourethane A) of the formula 1

$$R_n(OR^1)_{3-n}Si\text{---}R^2\text{---}NH\text{---}(C\text{=}O)\text{---}OR^3 \qquad \text{formula 1,}$$

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and
B) at least one diisocyanate B),
in a molar ratio of A) to B) of from 3:1 to 1.5:1;
C) optionally in the presence of at least one catalyst C), and
D) optional reaction of the residual amount of NCO groups of B) with an alcohol D).

13. The alkoxysilane-functionalized allophanate according to claim 12, wherein the component c) is selected from the group consisting of metal carboxylates, tert-amines, amidine, guanidine, quaternary ammonium salts, tetraalkylammonium salts, quaternary phosphonium salts, metal acetylacetonates, quaternary ammonium acetylacetonates, quaternary phosphonium acetylacetonates, alone or in a mixture.

14. The alkoxysilane-functionalized allophanate according to claim 12, wherein the component c) is zinc acetylacetonate and/or zinc ethylhexanoate.

15. The alkoxysilane-functionalized allophanate according to claim 12, wherein the alcohol D) is selected from methanol, ethanol, propanol, isopropanol, 1-butanol, 2-butanol, pentanol, ethyl-2-hexanol, 1-hexanol.

16. A method for preparing alkoxysilane-functionalized allophanates according to claim 12, by reacting
A) at least one alkoxysilane group-containing monourethane A) of the formula 1

$$R_n(OR^1)_{3-n}Si\text{---}R^2\text{---}NH\text{---}(C\text{=}O)\text{---}OR^3 \qquad \text{formula 1,}$$

where R, $R^1$, $R^2$ and $R^3$ are each independently hydrocarbyl radicals having 1-8 carbon atoms, which may be linear, branched or cyclic, or else may be integrated together to form a cyclic system, and n is 0-2, and
B) at least one diisocyanate B),
in a molar ratio of A) to B) of from 3:1 to 1.5:1;
C) optionally in the presence of at least one catalyst C), and
D) optional reaction of the residual amount of NCO groups of B) with an alcohol D).

17. The method according to claim 16, wherein the reaction is carried out at temperatures in the range from 15 to 40° C.

18. The method according to claim 16, wherein the reaction is carried out at temperatures in the range from 80 to 220° C.

19. The method according to claim 16, wherein the reaction of the residual amount of NCO groups of B) with an alcohol D) is carried out at temperatures in the range of 30-150° C.

20. The method according to claim 16, wherein the reaction is carried out in the presence of zinc acetylacetonate and/or zinc ethylhexanoate as catalyst C).

21. The method according to claim 16, wherein the residual amount of NCO groups of B) is reacted with an alcohol D) at the ratio of the NCO groups to OH groups of the alcohol D) of from 0.8:1 to 1.2:1.

* * * * *